United States Patent
Zhang et al.

(10) Patent No.: US 8,138,134 B2
(45) Date of Patent: Mar. 20, 2012

(54) QUATERNIZED CELLULOSE ETHERS FOR PERSONAL CARE PRODUCTS

(75) Inventors: Xiaodong Zhang, Livingston, NJ (US); Russell L. Kreeger, Flemington, NJ (US); Edward F. Diantonio, Staten Island, NY (US); Wing K. Li, East Brunswick, NJ (US); Tatiana Drovetskaya, Basking Ridge, NJ (US)

(73) Assignee: Union Carbide Chemicals & Plastics Technology LLC

( * ) Notice: Subject to any disclaimer, the term of this patent is extended or adjusted under 35 U.S.C. 154(b) by 0 days.

(21) Appl. No.: 12/443,333

(22) PCT Filed: Sep. 24, 2007

(86) PCT No.: PCT/US2007/079302
§ 371 (c)(1),
(2), (4) Date: Feb. 8, 2010

(87) PCT Pub. No.: WO2008/042635
PCT Pub. Date: Apr. 10, 2008

(65) Prior Publication Data
US 2010/0132132 A1    Jun. 3, 2010

Related U.S. Application Data

(60) Provisional application No. 60/848,550, filed on Sep. 29, 2006, provisional application No. 60/898,567, filed on Jan. 31, 2007.

(51) Int. Cl.
*C11D 1/37* (2006.01)
*C11D 1/94* (2006.01)
*C11D 3/22* (2006.01)

(52) U.S. Cl. ........ 510/125; 510/119; 510/123; 510/127; 510/130; 510/155; 510/426; 510/427; 510/428; 510/470; 510/473

(58) Field of Classification Search ............... 510/119, 510/123, 125, 127, 130, 155, 426, 427, 428, 510/470, 473
See application file for complete search history.

(56) References Cited

U.S. PATENT DOCUMENTS

| | | |
|---|---|---|
| 4,228,277 A | 10/1980 | Landoll |
| 4,663,159 A | 5/1987 | Brode, II et al. |
| 4,845,175 A | 7/1989 | Lo |
| 5,407,919 A | 4/1995 | Brode et al. |
| 5,866,110 A | 2/1999 | Moore et al. |
| 6,429,177 B1 | 8/2002 | Williams et al. |
| 6,673,124 B2 | 1/2004 | Laurent et al. |
| 2001/0021387 A1 | 9/2001 | Krammer et al. |
| 2002/0045684 A1 | 4/2002 | Bacher et al. |
| 2002/0195024 A1 | 12/2002 | Ayambem et al. |
| 2003/0130500 A1 | 7/2003 | Schlesiger et al. |
| 2006/0053565 A1* | 3/2006 | Cooke et al. .............. 8/115.51 |
| 2006/0191081 A1* | 8/2006 | Legrand et al. .............. 8/405 |
| 2006/0199742 A1* | 9/2006 | Arisz et al. .................. 507/114 |
| 2007/0031362 A1 | 2/2007 | Kreeger et al. |
| 2007/0258931 A1* | 11/2007 | Muller ..................... 424/70.7 |
| 2008/0233062 A1* | 9/2008 | Krishnan ..................... 424/59 |
| 2009/0031505 A1* | 2/2009 | Kravtchenko et al. ......... 8/407 |
| 2009/0041687 A1* | 2/2009 | Beumer et al. ............... 424/59 |
| 2009/0071369 A1* | 3/2009 | Ragone et al. ........... 106/169.01 |
| 2009/0182046 A1* | 7/2009 | Dierker et al. ............... 514/547 |
| 2009/0264585 A1* | 10/2009 | Avramidis et al. ............ 524/563 |
| 2010/0034761 A1* | 2/2010 | Fenyvesi et al. ............. 424/59 |

FOREIGN PATENT DOCUMENTS

| EP | 1311227 B1 | 9/2004 |
|---|---|---|
| WO | 2005000903 | 1/2005 |

* cited by examiner

*Primary Examiner* — Charles Boyer

(57) ABSTRACT

Quaternized cellulose ethers suitable for personal care products are described.

9 Claims, No Drawings

QUATERNIZED CELLULOSE ETHERS FOR PERSONAL CARE PRODUCTS

CROSS REFERENCE TO RELATED APPLICATIONS

This application is a 35 USC §371 national phase filing of PCT/US2007/079302 filed Sep. 24, 2007, which claims the benefit of U.S. Provisional Application Ser. No. 60/848,550, filed Sep. 29, 2006, and U.S. Provisional Application Ser. No. 60/898,567, filed Jan. 31, 2007.

FIELD

The present invention relates to quaternized cellulose ethers suitable for rheological modification of personal care products.

BACKGROUND

Generally, rheology modifiers are used to adjust a composition's rheological properties (including viscosity, flow rate, stability of viscosity over time or with increased temperature, and the composition's ability to suspend particles). For personal care products, the rheology of a formulation can have significant impact on consumer perceptions of the product. Known polymeric thickeners often show poor thickening efficiency or poor surfactant compatibility, and associative thickeners, while not suffering from these faults, display undesirable characteristics like reduced spreadability, poor viscosity maintenance at increased temperatures, and reduction of lather/foam.

Thus, a continuing need exists for new rheological modifiers that are efficient in thickening compositions for personal care products, while eliminating the typical shortcomings of currently known systems. Moreover, as sensory perception is critical in personal care product differentiation, it is important that said rheological modifiers maintain or even improve the feel of such products.

SUMMARY

In one embodiment, the present invention provides personal care compositions, comprising a combination of surfactants, comprising at least two of ammonium laureth sulfate, ammonium lauryl sulfate, sodium laureth sulfate, sodium lauryl sulfate, decylglucoside, and cocamidopropyl betaine; and at least one derivatized quaternized hydroxyethyl cellulose ether, wherein the quaternized cellulose ether comprises fewer than 4000 anhydroglucose repeat units, an average substitution level of hydrophobic substituents from about 0.005 to about 0.3 moles of substituent per mole of anhydroglucose unit, a nitrogen percentage from about 0.3 to about 3.0, provided that the average substitution level of hydrophobic substituents is less than the average substitution level of cationic substituents.

In another embodiment, the present invention provides methods for increasing viscosity of a personal care composition including a combination of surfactants without concomitant increases in stringiness and reduced spreadability, comprising combining with the personal care composition at least one derivatized quaternized hydroxyethyl cellulose ether, wherein the quaternized cellulose ether comprises fewer than 4000 anhydroglucose repeat units, an average substitution level of hydrophobic substituents from about 0.005 to about 0.3 moles of substituent per mole of anhydroglucose unit, a nitrogen percentage from about 0.3 to about 3.0, provided that the average substitution level of hydrophobic substituents is less than the average substitution level of cationic substituents.

DETAILED DESCRIPTION

In one embodiment, the present invention provides personal care compositions, comprising a combination of surfactants, comprising at least two of ammonium laureth sulfate, ammonium lauryl sulfate, sodium laureth sulfate, sodium lauryl sulfate, decylglucoside, and cocamidopropyl betaine; and at least one derivatized quaternized hydroxyethyl cellulose ether, wherein the quaternized cellulose ether comprises fewer than 4000 anhydroglucose repeat units, an average substitution level of hydrophobic substituents from about 0.005 to about 0.3 moles of substituent per mole of anhydroglucose unit, a nitrogen percentage from about 0.3 to about 3.0, provided that the average substitution level of hydrophobic substituents is less than the average substitution level of cationic substituents.

In another embodiment, the present invention provides methods for increasing viscosity of a personal care composition including a combination of surfactants without concomitant increases in stringiness and reduced spreadability, comprising combining with the personal care composition at least one derivatized quaternized hydroxyethyl cellulose ether, wherein the quaternized cellulose ether comprises fewer than 4000 anhydroglucose repeat units, an average substitution level of hydrophobic substituents from about 0.005 to about 0.3 moles of substituent per mole of anhydroglucose unit, a nitrogen percentage from about 0.3 to about 3.0, provided that the average substitution level of hydrophobic substituents is less than the average substitution level of cationic substituents.

"Quaternized cellulose ethers" refers to cellulose ether derivatives containing quaternary ammonium groups. Generally, the cellulose ether component comprises anhydroglucose repeat units derivatized with certain ethers. For example, the term "M.S. (hydroxyethyl)" designates the average number of moles of hydroxyethyl groups which have been attached by an ether linkage per mole of anhydroglucose unit. Preferably, cellulose ethers used to make quaternized cellulose ethers of the present invention have an M.S. (hydroxyethyl) of from 1.0 to 3.5, more preferably from 1.5 to 2.5, more preferably from 1.8 to about 2.4, most preferably from about 2.0 to about 2.2. In one embodiment, the quaternized cellulose ethers of the present invention have a nitrogen percentage (% N–average weight percent of nitrogen per anhydroglucose repeat unit) from about 0.3 to about 3.0.

The cellulose ethers used to make quaternized cellulose ethers of the present invention generally have at least 250 anhydroglucose repeat units, preferably at least 350 anhydroglucose repeat units. In a further embodiment, the cellulose ethers have fewer than 4000 anhydroglucose repeat units, preferably fewer than 3750, preferably fewer than 3500, preferably fewer than 3250, preferably fewer than 3000, preferably fewer than 2500 and more preferably fewer than 2000 anhydroglucose repeat units. Such cellulose ethers are readily commercially available. Alternatively, such cellulose ethers can be prepared from cellulose by methods known to those skilled in the art.

Typical cellulose ethers include for example, hydroxyethyl cellulose, hydroxypropyl cellulose, methyl cellulose, hydroxypropyl methyl cellulose, hydroxyethyl methyl cellulose or hydroxyethyl carboxylmethyl cellulose. Preferred cellulose ethers include hydroxyethyl cellulose and hydroxypropyl cellulose. The most preferred cellulose ethers suitable for preparing the quaternized cellulose ethers comprise hydroxyethyl groups.

The above cellulose ethers are derivatized with a hydrophobic substituent and a cationic nitrogen-containing substituent to form quaternized cellulose ethers of the present invention.

In one embodiment, the hydrophobic substituent has the formula (I):

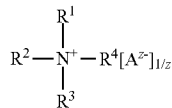

(I)

wherein $R^1$ and $R^2$ are each, independently, methyl or ethyl, $R^3$ is —$CH_2$—CHOH—$CH_2$— or —$CH_2CH_2$—, $R^4$ is an alkyl, alkylaryl or arylalkyl group having at least 8 carbon atoms, preferably 8 to 30 carbon atoms, preferably from 10 to 30 carbon atoms, more preferably from 12 to 24 carbon atoms, and most preferably from 12 to 18 carbon atoms, $A^{z-}$ is an anion, and z is 1, 2 or 3. In one embodiment, the hydrophobic substituent is derived from glycidyl ethers, such as nonylphenyl glycidyl ether or dodecylphenyl glycidyl ether; or alpha-olefin epoxides, such as 1,2-epoxy hexadecane and their respective chlorohydrins, or alkyl halides, e.g., dodecyl bromide, and mixtures thereof. Preferably, both $R^1$ and $R^2$ are methyl. Preferably, $R^3$ is —$CH_2$—CHOH—$CH_2$—. Preferably, $R^4$ is —$C_nH_{(2n+1)}$, where n is from 8 to 30, more preferably n is 12. The most preferred aliphatic $R^4$ is the dodecyl group, which is most preferably straight-chained. Preferably, $A^{z-}$ is phosphate, nitrate, sulfate or halide, most preferably chloride. Preferably, z is 1 or 2, most preferably 1. Preferably, the average substitution level of the hydrophobic substituent is from about 0.005 to about 0.3, more preferably from about 0.01 to about 0.2, more preferably from about 0.02 to about 0.15 mole or from about 0.01 to about 0.1 moles of substituent per mole of anhydroglucose unit. Methods for derivatizing cellulose ethers to comprise such hydrophobic substituents are known to those skilled in the art, see for example, U.S. Pat. Nos. 4,228,277, 4,663,159, and 4,845,175, which are incorporated by reference herein.

The cationic nitrogen containing substituent basically has the formula (I) above, except that $R^4$ is now methyl or ethyl instead of a hydrophobic group. In one embodiment, the average substitution level of the cationic substituent is from about 0.005 to about 0.7 moles of the substituent per mole of anhydroglucose unit, preferably from about 0.01 to about 0.5 moles, more preferably from about 0.02 to about 0.35 moles, most preferably from about 0.025 to about 0.2 moles. Methods for derivatizing cellulose ethers to contain such cationic substituents are known to those skilled in the art, see for example, U.S. Pat. No. 4,663,159.

In one embodiment, the quaternized cellulose ether is a hydroxyethyl cellulose ether. Preferably the hydroxyethyl cellulose ether has a 2 wt. % Brookfield viscosity greater than 500 cps, more preferably greater than 1000 cps, more preferably greater than 2000 cps, more preferably greater than 3000 cps, and most preferably greater than 4000 cps. Preferably, this derivatized quaternized hydroxyethyl cellulose ether comprises fewer than 4000 anhydroglucose repeat units, has an average substitution level of hydrophobic substituents from about 0.005 to about 0.3 moles of substituent per mole of anhydroglucose unit, and a nitrogen percentage from about 0.3 to about 3.0, provided that the average substitution level of hydrophobic substituents is less than the average substitution level of cationic substituents.

Such a quaternized hydroxyethyl cellulose ether has a relatively high molecular weight. It is well known in the art that higher molecular weight cellulose ethers tend to be stringy.

In a preferred embodiment, the quaternized cellulose ether is of the formula (II):

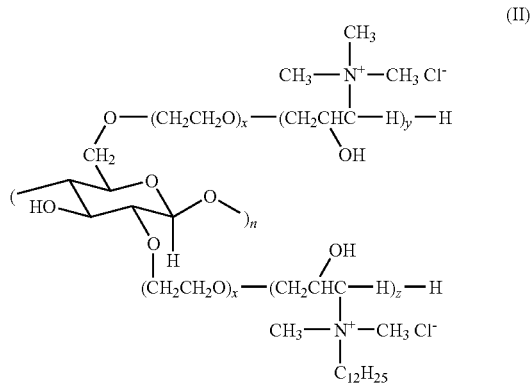

(II)

wherein n is about 500 to about 2000, x is chosen such that the hydrophobic substitution M.S.(hydroxyethyl) is about 2.1 and y and z are chosen such that the quaternized cellulose ether has percent nitrogen of about 0.05 to about 3.5.

The appropriate concentration of quaternized cellulose ethers of the invention for use in a personal care product will depend on various parameters, including the particular personal care product being formulated, and the desired viscosity. As will be seen by the following examples, however, the compositions of the invention provide greater thickening efficiency as compared to previous compositions. Preferably a concentration of about 0.02% to about 1.0% by weight, more preferably about 0.05% to about 0.5% by weight, of the quaternized cellulose ether of the invention based on the total weight of the personal care composition is used.

"Personal care" refers to compositions that are to be topically applied to a person. Examples of personal care compositions include skin care and cosmetic products (e.g., facial cream, moisturizers, cleansers, lotions, night creams, sunscreens, tanning, foundation, mascara, eye-liner, lipstick, and the like), nail care products (such as polish and conditioners), toothcare products (e.g., toothpaste and rinses), and hair care products (including styling gels and hairsprays). "Personal care actives" are components that impart a specific performance property to a personal care composition. Examples of personal care actives include vitamins, silicone oils, sun screens, as well as solvents, diluents, and adjuvants such as water, ethyl alcohol, isopropyl alcohol, higher alcohols, glycerin, propylene glycol, sorbitol, preservatives, surfactants, menthol, eucalyptus oil, other essential oils, fragrances or viscosity adjusters. Such personal care products are commercially available and known to those skilled in the art.

The quaternized cellulose ethers described herein provide favorable rheological modification properties when formulated in personal care products, including high thickening efficiency at low concentrations with reduced viscosity loss with increasing temperature. The formulations containing these polymers also show reduced stringiness and improved spreadablity compared to other associative thickeners. The quaternized cellulose ethers also provide personal care products with improved skin and hair sensory appeal and lather performance (e.g., increased foam). Improved properties include improved softness, smoothness, silkiness, moisturizing, and/or wet and dry combing properties.

It should be understood that the quaternized cellulose ethers of the present invention are cosmetically acceptable, that is, no more toxic, irritating, or unpleasant smelling when present in the amounts typically found in personal care compositions than any other typical personal care ingredients.

The quaternized cellulose ethers of the present invention comprise both the hydrophobic substituent and the cationic substituent, advantageously in the preferred weight ranges disclosed above. The hydrophobic substituent and the cationic substituent can be reacted with the cellulose ether in any order or simultaneously in a known manner. Preferably, the reaction is carried as described in U.S. Pat. No. 5,407,919 or WO 2005/000903, while adapting the molar ratio between the cellulose ether and hydrophobic substituent and the cationic substituent to the desired substitution levels. Preferably, the molar ratio between the hydrophobic substituent and the anhydroglucose units of the cellulose ether is from 0.002 to 0.4, more preferably from 0.02 to 0.2. Preferably, the molar ratio between the cationic substituent and the anhydroglucose units of the cellulose ether is from 0.05 to 2.0, more preferably from 0.2 to 0.7.

It should be noted that the quaternized cellulose ethers which are used in the compositions and the methods of the present invention, derivatized quaternized hydroxyethyl cellulose ethers, wherein the quaternized cellulose ether comprises fewer than 4000 anhydroglucose repeat units, and the average substitution level of hydrophobic substituents is less than the average substitution level of cationic substituents, have a different structure than commercially available quaternized cellulose ethers. For example, SOFTCAT™ Polyquaternium-67, available from Amerchol Corporation, has more than 4000 anhydroglucose repeat units. This quaternized cellulose ether has been used in personal care products with great success in the past as a conditioner, however, it has not shown any rheological modification properties.

The cationic associative polymer disclosed in U.S. Pat. No. 6,673,124, specifically the quaternized laurylhydroxyethylcellulose which is sold under the name QUATRISOFT LM 200 by Amerchol Corporation, is a quaternized cellulose ether with fewer than 4000 anhydroglucose repeat units, however, it has an average substitution level of hydrophobic substituents that is equal to or greater than the average substitution level of cationic substituents. As shown in the attached examples, no rheological modification property has been observed for this polymer either.

The quaternized cellulose ethers which are used in the present invention are typically water-soluble. As used herein, the term "water-soluble" means that at least 1 gram, and preferably at least 2 grams of the cellulose ether derivative are soluble in 100 grams of distilled water at 25° C. and 1 atmosphere. The extent of water-solubility can be varied by adjusting the extent of ether substitution on the cellulose ether and by adjusting the substitution level of the hydrophobic substituent and the cationic substituent. Techniques for varying the water solubility of cellulose ethers are known to those skilled in the art.

The following examples are presented to illustrate the invention and are not to be interpreted as limiting it. All percentages, parts and ratios are by weight unless otherwise stated.

EXAMPLES

Example 1

Quaternized cellulose ethers of the present invention are the result of combining the following components listed in TABLE 1:

TABLE 1

| | Batch 1 | Batch 2 | Batch 3 (Comparative) | Batch 4 | Batch 5 (Comparative) | Batch 6 | Batch 7 |
|---|---|---|---|---|---|---|---|
| HEC 1 | 60 | — | — | — | — | — | — |
| HEC 2 | — | 80 | 40 | — | 300 | 40* | 80 |
| HEC 3 | — | — | — | 60 | — | — | — |
| Acetone | 360 | 480 | 240 | — | — | — | 460 |
| 60% aqueous isopropyl alcohol (IPA) | — | — | — | — | 1805 | — | — |
| 10% aqueous IPA | — | — | — | — | — | 241 | — |
| 12% aqueous IPA | — | — | — | 360 | — | — | — |
| 25 weight % aqueous soln. of sodium hydroxide (NaOH) (calc as dry wt) | 4.9 | 9.25 | 5.2 | 2.85 | 27 | 2.45 | 7.2 |
| QUAB 342 | 28 | 60 | 35 | 10 | 150 | 10 | 40 |
| QUAB 151 | 3.0 | 15 | 0 | 12 | 0 | 5 | 4 |

*Batch 5 used in place of HEC

The above abbreviations are defined as follows:

HEC-1: A hydroxyethyl cellulose having a viscosity of about 200 cps (mPas), about 500 anhydroglucose repeat units and an average number of moles of hydroxyethyl groups per mole of anhydroglucose unit, designated as M.S.(hydroxyethyl), of about 2.2. The molecular weight of the hydroxyethyl cellulose below is given as viscosity measured as a 5 weight percent aqueous solution at 25° C. using a Brookfield LVT viscometer. This hydroxyethyl cellulose is commercially available as CELLOSIZE™ QP-3L hydroxyethyl cellulose (HEC) from The Dow Chemical Company.

HEC-2: A hydroxyethyl cellulose having a viscosity of about 500 cps (mPas), about 1500 anhydroglucose repeat units and an average number of moles of hydroxyethyl groups per mole of anhydroglucose unit, designated as M.S. (hydroxyethyl), of about 2.0. The molecular weight of the hydroxyethyl cellulose below is given in viscosity measured as a 2 weight percent aqueous solution at 25° C. using a Brookfield LVT viscometer. This hydroxyethyl cellulose is commercially available as CELLOSIZE™ QP-300 hydroxyethyl cellulose (HEC) from The Dow Chemical Company.

HEC-3: A hydroxyethyl cellulose having a viscosity of about 5000 cps (mPa's), about 2000 anhydroglucose repeat units and an average number of moles of hydroxyethyl groups per mole of anhydroglucose unit, designated as M.S. (hydroxyethyl), of about 2.0. The molecular weight of the hydroxyethyl cellulose below is given in viscosity measured as a 2 weight percent aqueous solution at 25° C. using a Brookfield LVT viscometer. This hydroxyethyl cellulose is commercially available as CELLOSIZE™ QP-4400 hydroxyethyl cellulose (HEC) from The Dow Chemical Company.

Cationic substituent: A 70 weight percent aqueous solution of 2,3-epoxypropyltrimethyl ammonium chloride, commercially available from Degussa Corporation as QUAB™ 151. This contributes a cationic moeity to the cellulose ether.

Hydrophobic substituent: A 40 weight percent aqueous solution of 3-chloro-2-hydroxypropyldodecyldimethyl ammonium chloride, commercially available from Degussa Corporation as QUAB™ 342. This contributes one hydrophobic moeity and one cationic moeity to the cellulose ether.

A reaction vessel equipped with a stirrer, condenser, addition funnels, and nitrogen supply is charged with HEC (as listed) and acetone or IPA. The system is purged with nitrogen. An aqueous solution of sodium hydroxide (for Batch 1, 4.9 g dry/0.12 mol) is added drop wise via syringe. After stirring for 30 minutes at ambient temperature, QUAB 342 is added drop wise. Then QUAB 151 is added drop wise. The slurry is heated to 55° C. over 30 minutes. After holding for 3 hours, the slurry is cooled to less than 40° C. and neutralized with 2.7 g acetic acid. The slurry is transferred and washed three times with a mixture of 80 weight percent acetone and 20 weight percent water, once with a mixture of 90 weight percent isopropyl alcohol and 10 weight percent water, and once with acetone containing a small amount of glyoxal and acetic acid. After drying in a vacuum oven at about 30-35° C., the product is passed through a 30-mesh sieve screen and analyzed.

Example 2

Substantially following the protocol of Example 1, the batches listed in TABLE 1 were prepared and characterized. The results are listed in TABLE 2:

TABLE 2

| Batch | % N | Hydrophobic Substitution | Cationic Contribution from QUAB 151 | Total Cationic Substitution | Viscosity (%) |
|---|---|---|---|---|---|
| 1 | 0.83 | 0.12 | 0.05 | 0.17 | 7400 (5) |
| 2 | 1.09 | 0.07 | 0.15 | 0.22 | 360 (2) |
| 3 (Comp.) | 0.42 | 0.09 | 0 | 0.09 | 2300 (2) |
| 4 | 1.02 | 0.02 | 0.18 | 0.20 | 5100 (2) |
| 5 (Comp.) | 0.21 | 0.04 | 0 | 0.04 | 590 (2) |
| 6 | 1.00 | 0.06 | 0.14 | 0.20 | 685 (2) |
| 7 | 0.47 | 0.04 | 0.05 | 0.09 | 240 (2) |

Batches 1-7 can be represented by the formula (II) above, wherein n is about 500-2000, x is chosen that the hydroxyethyl substitution M.S. is about 2.0 to 2.4 and y and z are chosen such that the batches have the levels of percent nitrogen and hydrophobic substitution (HS) listed in TABLE 2. Nitrogen content, % N: The average weight percent of nitrogen per anhydroglucose repeat unit is determined analytically by using an automated Buchi Kjeldahl distillation unit and titrating with an automated titrimeter. The average number of moles of the hydrophobic substituent per mole of anhydroglucose unit is designated as hydrophobic substitution (HS). The HS is measured using nuclear magnetic resonance (1H-NMR, 400 MHz, sodium trimethylsilyl propionate as a standard and deuterium oxide as a solvent at room temperature). The average number of moles of the cationic substituent per mole of anhydroglucose unit is designated as cationic substitution (CS) and is measured using nuclear magnetic resonance (1H-NMR, 400 MHz, sodium trimethylsilyl propionate as a standard and deuterium oxide as a solvent at room temperature) and/or by calculating the difference between the total nitrogen content and the nitrogen content due to the HS. For example, the HS was determined by % N for those examples in which only QUAB 342 was used and for the others where both QUAB 342 and QUAB 151 were used, the examples were run first with only QUAB 342 to determine the % N incorporation and the HS, and then the examples were run with both QUAB 342 and QUAB 151. The % N and CS from the QUAB 151 were calculated by subtracting the % N due to the QUAB 342 from the reference run from the total nitrogen. Viscosity 2 or 5 percent: The viscosity of a 2 or 5 weight percent aqueous solution at 25° C. is measured using a Brookfield LTV viscometer at 30 rpm (revolutions per minute) and spindle No. 2, 3, or 4. Unless otherwise indicated, viscosity is given in centipoises (cPs).

Example 3

Personal care compositions of the present invention include quaternized cellulose ethers from Example 1, having the components recited in TABLE 3:

TABLE 3

|  | Batch A | Batch B | Batch D |
|---|---|---|---|
| Ammonium laureth sulfate (ALS) (28% active) | 20.9% | 20.9% | 20.9% |
| Sodium laureth sulfate, 2 mole ethoxylate (ES-2) (26% active) | 10.1% | 10.1% | 10.1% |
| Cocamidopropyl betaine (CAPB) (35% active) | 6.7% | 6.7% | 6.7% |
| Salt | 0.5% | 0.5% | 0.5% |
| Batch 1 | 0.2% | — | — |
| Batch 2 | — | 0.2% | — |
| Batch 6 | — | — | 0.2% |
| Water | Balance | Balance | Balance |

Example 4 (Comparative)

Comparative personal care compositions have the components recited in TABLE 4:

TABLE 4

|  | Batch C (Comp.) | Batch E (Comp.) |
|---|---|---|
| Ammonium laureth sulfate (ALS) (28% active) | 20.9% | 20.9% |
| Sodium laureth sulfate, 2 mole ethoxylate (ES-2) (26% active) | 10.1% | 10.1% |
| Cocamidopropyl betaine (CAPB) (35% active) | 6.7% | 6.7% |

TABLE 4-continued

|  | Batch C (Comp.) | Batch E (Comp.) |
|---|---|---|
| Salt | 0.5% | 0.5% |
| GLUCAMATE ™ DOE-120 PEG-120 Methyl Glucose Dioleate (Noveon) | — | 1% |
| Batch 3 (Comparative) | 0.2% | — |
| Water | Balance | Balance |

Example 5

Personal care compositions were made substantially according to the protocols of Examples 3 and 4, and were tested as noted.

All viscosity measurements were conducted with Brookfield LVT viscosity at 22° C. The results are summarized in TABLE 5.

TABLE 5

|  | HS | N % | Viscosity (cps) |
|---|---|---|---|
| Batch A | 0.12 | 0.83 | 55,000 |
| Batch B | 0.07 | 1 | 55,000 |
| Batch C (comparative) | 0.086 | 0.42 | 100,000 |
| Batch D | 0.04 | 0.94 | 12,800 |
| Batch E (comparative) | — | — | 7,000 |

It can be clearly seen from the data in the above table that the hydrophobically modified cationic HECs provide much better thickening efficiency than DOE-120 material, even when five times more DOE-120 is used.

A body wash panel study was conducted with 10 panelists. The percent of panelists that preferred the specific formulation for each criteria is noted in TABLE 6:

TABLE 6

|  | Batch A | Batch E (comparative) |
|---|---|---|
| Foam volume | 70 | 30 |
| Foam feel | 70 | 30 |
| Wet feel | 80 | 20 |
| Dry feel | 100 | 0 |

The data clearly indicates that a personal care composition of present invention provides significantly better skin feel properties.

Example 6

Personal care compositions were prepared substantially according to the above described protocols, and having the components recited in TABLE 7:

TABLE 7

|  | Batch F | Batch G (comparative) |
|---|---|---|
| Sodium laureth sulfate, 2 mole ethoxylate (ES-2) (26% active) | 42.3% | 42.3% |
| Cocamidopropyl betaine (CAPB) (35% active) | 11.4% | 11.4% |
| Batch 1 | 0.2% | — |
| GLUCAMATE ™ DOE-120 PEG-120 Methyl Glucose Dioleate (Noveon) | — | 1% |
| Water | Balance | Balance |

All viscosities were measured with CA Instruments Rheometer with Couette geometry at shear rate of 0.5 second$^{-1}$. Data are summarized in the Table 8:

TABLE 8

| Temperature (° C.) | Batch F | Batch G (comparative) |
|---|---|---|
| 25 | 38000 | 30000 |
| 30 | 22000 | 12000 |
| 35 | 11000 | 4800 |
| 40 | 5500 | 1100 |

The data shows that the hydrophobically modified cationic HEC containing formulation can maintain viscosity much better than the DOE-120 containing formulation at higher temperatures such as 40° C.

The formulations were tested for product aesthetics by panel study. Four panelists were asked to give product aesthetics scores on these two formulations on 1-5 scale (5 being the best). Features such as ease-of-spreading and stringiness were part of the product aesthetics evaluation. The average score for Batch F was 4, while the average score for the comparative Batch G was 2, with Batch F showing a clear advantage in ease-of-spreading in particular.

Example 7

Personal care compositions of the present invention (oxidative dye compositions) have the components recited in TABLE 9:

TABLE 9

|  |  | Batch H (control) | Batch I (comparative) | Batch J (comparative) | Batch K |
|---|---|---|---|---|---|
| Oxidation Dye Precursor (g) | Deionized water | 47.34 | 27.34 | 37.34 | 27.34 |
|  | EMULGEN BL-309 Deceth-3 | 9.00 | 9.00 | 9.00 | 9.00 |
|  | JEECOL O olelyl alcohol | 6.00 | 6.00 | 6.00 | 6.00 |
|  | EMERSOL 213 oleic acid | 3.00 | 3.00 | 3.00 | 3.00 |
|  | PLANTAREN 1200 alkyl polyglucoside | 6.90 | 6.90 | 6.90 | 6.90 |
|  | Ethanol (100%) | 6.50 | 6.50 | 6.50 | 6.50 |
|  | EGMBE ethylene glycol mono butyl ether | 10.00 | 10.00 | 10.00 | 10.00 |

TABLE 9-continued

|  |  | Batch H (control) | Batch I (comparative) | Batch J (comparative) | Batch K |
|---|---|---|---|---|---|
|  | GLUCAMATE LT (as 2% aqueous solution) | — | 10.00 | — | — |
|  | QUATRISOFT LM-200 (as 2% aqueous solution) | — | — | 10.00 | — |
|  | Batch 7 from Example 1 (as 2% aqueous solution) | — | — | — | 10.00 |
|  | Ammonia (20% aqueous solution) | 10.00 | 10.00 | 10.00 | 10.00 |
|  | RODOL RS TECH-3 Dihydroxybenzene | 0.40 | 0.40 | 0.40 | 0.40 |
|  | RODOL EG 3 Aminophenol | 0.07 | 0.07 | 0.07 | 0.07 |
|  | RODOL 24 DAPE 1, (beta-hydroxyethoxy)-2,4 diaminobenzene dichlorohydrate | 0.01 | 0.01 | 0.01 | 0.01 |
|  | RODOL MRP 1,3-dihydroxy-2-methylbenzene | 0.15 | 0.15 | 0.15 | 0.15 |
|  | RODOL D p-phenylenediamine | 0.63 | 0.63 | 0.63 | 0.63 |
| Oxidative Developer (g) | Hydrogen peroxide (6% aqueous solution) | 100 | 100 | 100 | 100 |

"Deceth-3" is the polyethylene glycol ether of decyl alcohol, conforming to the formula $CH_3(CH_2)_8CH_2(OCH_2CH_2)_nOH$ (where n has an average value of 3), available from Sidobre Sinnova. Oxidation dye compositions are prepared by adding the oxidative developer to the oxidative dye precursor and shaking vigorously.

The viscosities of the resulting dyeing compositions were measured at 25° C. using a Brookfield LTV viscometer at 10 rpm (revolutions per minute) and spindle No. 4. The results illustrate that the polymer of the invention (Batch K) provided excellent thickening efficiency in the oxidation dye composition (viscosity 9600 cps), while GLUCAMATE LT ("LT") showed no thickening benefit (1400 cps as compared to the control 2200 cps). QUATRISOFT LM-200 ("LM-200") was significantly less efficient (6200 cps). Efficient thickening is an essential attribute of oxidative dye compositions, as it keeps the colorant product on the application area and prevents it from running onto the face or outside the desired color zones.

Example 8

Personal care compositions of the present invention (oxidative dye compositions) have the components recited in TABLE 10:

TABLE 10

|  | Batch L (wt %) | Batch M (wt %) (comparative) |
|---|---|---|
| Ammonium laureth sulfate (ALS) | 20.9 | 20.9 |
| SLES-2 Sodium Laureth Sulfate | 10.1 | 10.1 |
| Cocamidopropyl betaine (CAPB) | 6.7 | 6.7 |
| NaCl solution | 2.5 | 2.5 |
| GLYDANT DMDM Hydantoin | 0.4 | 0.4 |
| Batch 2 | 20 | 0 |
| QP-100M hydroxyethyl cellulose polymer | 0 | 20 |

TABLE 10-continued

|  | Batch L (wt %) | Batch M (wt %) (comparative) |
|---|---|---|
| Water | 39.4 | 39.4 |
| Formulation viscosity (cp) | 74370 | 80120 |
| Stringiness | 1 | 2 |

QP-100M is a commercially available hydroxyethyl cellulose polymer containing at least 5000 anhydroglucose units. The viscosity for QP-100MH is typically about 5,500 cps for a 1% solution. % N is 1. The hydrophobic substitution level is 0.04.

While the viscosities achieved are comparable, the inventive batch displayed less stringiness. The relative stringiness of each formulation is evaluated on a scale of 1 to 5, with 5 being the most stringy, and 1 being the least stringy.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:
1. A personal care composition, comprising:
a combination of surfactants, comprising at least two of ammonium laureth sulfate, sodium laureth sulfate, and cocamidopropyl betaine; and
at least one derivatized quaternized hydroxyethyl cellulose ether, selected such that the quaternized cellulose ether comprises fewer than 4000 anhydroglucose repeat units, an average substitution level of hydrophobic substituents, comprising an alkyl, alkylaryl or arylalkyl group having 8 to 30 carbon atoms, from about 0.005 to about

0.3 moles of substituent per mole of anhydroglucose unit, a nitrogen percentage from about 0.3 to about 3.0, provided that the average substitution level of hydrophobic substituents is less than the average substitution level of cationic substituents; and with the proviso that the personal care composition does not contain methyl glucose dioleate.

2. The personal care composition of claim 1, wherein the hydrophobic substituent of the derivatized quaternized cellulose ether corresponds to the formula (I):

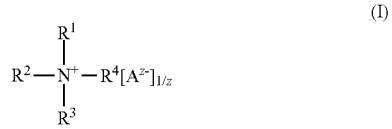

wherein:
$R^1$ and $R^2$ are each, independently, methyl or ethyl;
$R^3$ is —$CH_2$—CHOH—$CH_2$— or —$CH_2CH_2$—;
$R^4$ is an alkyl, alkylaryl or arylalkyl group having 8 to 30 carbon atoms;
$A^{z-}$ is an anion, and
z is 1, 2 or 3.

3. The personal care composition of claim 2, wherein $R^4$ is a dodecyl group.

4. The personal care composition of claim 1, wherein the hydrophobic substituent of the derivatized quaternized cellulose ether is derived from glycidyl ethers, alpha-olefin epoxides, alkyl halides, or mixtures thereof.

5. The personal care composition of claim 1, wherein the average substitution level of hydrophobic substituents on the derivatized quaternized cellulose ether is from about 0.01 to about 0.2 moles of substituent per mole of anhydroglucose unit.

6. The personal care composition of claim 1, wherein the average substitution level of the cationic substituent on the derivatized quaternized cellulose ether is from about 0.005 to about 0.7 moles of the substituent per mole of anhydroglucose unit.

7. The personal care composition of claim 1, wherein the hydroxyethyl cellulose has an average number of moles of hydroxyethyl groups per mole of anhydroglucose unit of about 2.0 to about 2.2.

8. The personal care composition of claim 1, wherein the 2 wt. % Brookfield viscosity is greater than 2000 cps, preferably greater than 3000 cps, and more preferably greater than 4000 cps.

9. A method for increasing the viscosity of a personal care composition comprising at least two of ammonium laureth sulfate, sodium laureth sulfate, and cocamidopropyl betaine without concomitant increases in stringiness and reduced spreadability, comprising:

selecting for addition to such personal care composition at least one derivatized quaternized hydroxyethyl cellulose ether, wherein the quaternized cellulose ether comprises fewer than 4000 anhydroglucose repeat units, an average substitution level of hydrophobic substituents, comprising an alkyl, alkylaryl or arylalkyl group having 8 to 30 carbon atoms, from about 0.005 to about 0.3 moles of substituent per mole of anhydroglucose unit, a nitrogen percentage from about 0.3 to about 3.0, provided that the average substitution level of hydrophobic substituents is less than the average substitution level of cationic substituents; and combining the derivatized quaternized hydroxyethyl cellulose ether with the personal care composition, provided that the personal care composition does not contain methyl glucose dioleate.

* * * * *